United States Patent
King et al.

(10) Patent No.: US 12,053,779 B2
(45) Date of Patent: Aug. 6, 2024

(54) SYSTEM AND METHOD FOR SEPARATION OF BLOOD COMPONENTS

(71) Applicant: ZOETIS SERVICES LLC, Parsippany, NJ (US)

(72) Inventors: William King, Warsaw, IN (US); Michael D. Leach, Warsaw, IN (US)

(73) Assignee: Zoetis Services LLC, Parsippany, NJ (US)

( * ) Notice: Subject to any disclaimer, the term of this patent is extended or adjusted under 35 U.S.C. 154(b) by 872 days.

(21) Appl. No.: 16/667,983

(22) Filed: Oct. 30, 2019

(65) Prior Publication Data

US 2021/0129132 A1 May 6, 2021

(51) Int. Cl.
*B01L 3/00* (2006.01)
*A61L 27/36* (2006.01)

(52) U.S. Cl.
CPC ........... *B01L 3/508* (2013.01); *A61L 27/3616* (2013.01); *B01L 2300/041* (2013.01); *B01L 2300/06* (2013.01); *B01L 2300/0832* (2013.01)

(58) Field of Classification Search
CPC .............. B01L 3/508; B01L 2300/041; B01L 2300/06; B01L 2300/0832; B01L 2300/042; B01L 2300/046; B01L 3/5082; A61L 27/3616
USPC ....................................................... 424/530
See application file for complete search history.

(56) References Cited

U.S. PATENT DOCUMENTS

| | | | |
|---|---|---|---|
| 3,792,699 A * | 2/1974 | Tobin | .............. B01L 3/5029 401/133 |
| 3,902,964 A | 9/1975 | Greenspan | |
| 4,409,106 A | 10/1983 | Furuta et al. | |
| 6,531,321 B1 | 3/2003 | Ryan et al. | |
| 9,649,424 B2 | 5/2017 | Sato et al. | |
| 2005/0170327 A1 | 8/2005 | Sumida et al. | |
| 2006/0175242 A1 | 8/2006 | Dorian et al. | |
| 2007/0253940 A1 | 11/2007 | Sumida et al. | |

(Continued)

FOREIGN PATENT DOCUMENTS

| | | |
|---|---|---|
| AU | 2017340091 | 4/2018 |
| EP | 0248524 | 12/1987 |

(Continued)

OTHER PUBLICATIONS

The Hydrodynamic Radii of Macromolecules and Their Effect on Red Bloom Cell Aggregation; Department of Physiology and Biophysics, Keck School of Medicine, University of SoCal; Published Sep. 8, 2004.

(Continued)

*Primary Examiner* — Jill A Warden
*Assistant Examiner* — Jacqueline Brazin
(74) *Attorney, Agent, or Firm* — Scott C. Mayhew

(57) ABSTRACT

In some forms, the present disclosure provides systems and methods for isolation of platelet rich plasma from a liquid tissue sample. In accordance with some forms of the disclosed systems and methods, provide rapid separation of blood components with the need for centrifugation. Accordingly, in one embodiment, the present disclosure provides a method for isolating platelet rich plasma, the method comprising combining a liquid tissue sample with a polymer composition, the polymer composition comprising polyethylene glycol.

7 Claims, 2 Drawing Sheets

(56) References Cited

U.S. PATENT DOCUMENTS

| | | | |
|---|---|---|---|
| 2009/0220482 A1* | 9/2009 | Higgins | A61K 45/06 424/94.64 |
| 2010/0151438 A1 | 6/2010 | Liming et al. | |
| 2014/0056989 A1 | 2/2014 | Weissman et al. | |
| 2018/0070581 A1 | 3/2018 | Tarrand et al. | |
| 2019/0134293 A1 | 5/2019 | Chang et al. | |

FOREIGN PATENT DOCUMENTS

| | | |
|---|---|---|
| EP | 0325413 | 7/1989 |
| EP | 0597577 | 5/1994 |
| EP | 1547606 | 6/2005 |
| EP | 1723959 | 11/2006 |
| JP | 11285607 | 10/1999 |
| WO | WO2018066167 | 4/2018 |

OTHER PUBLICATIONS

Platelet Separation From Whole Blood in an Aqueous Two-Phase System with Water-Soluble Polymers, Journal of Pharmacological Sciences, 2006, The Japanese Pharmacological Society, 101, 91-97 (2006).

* cited by examiner

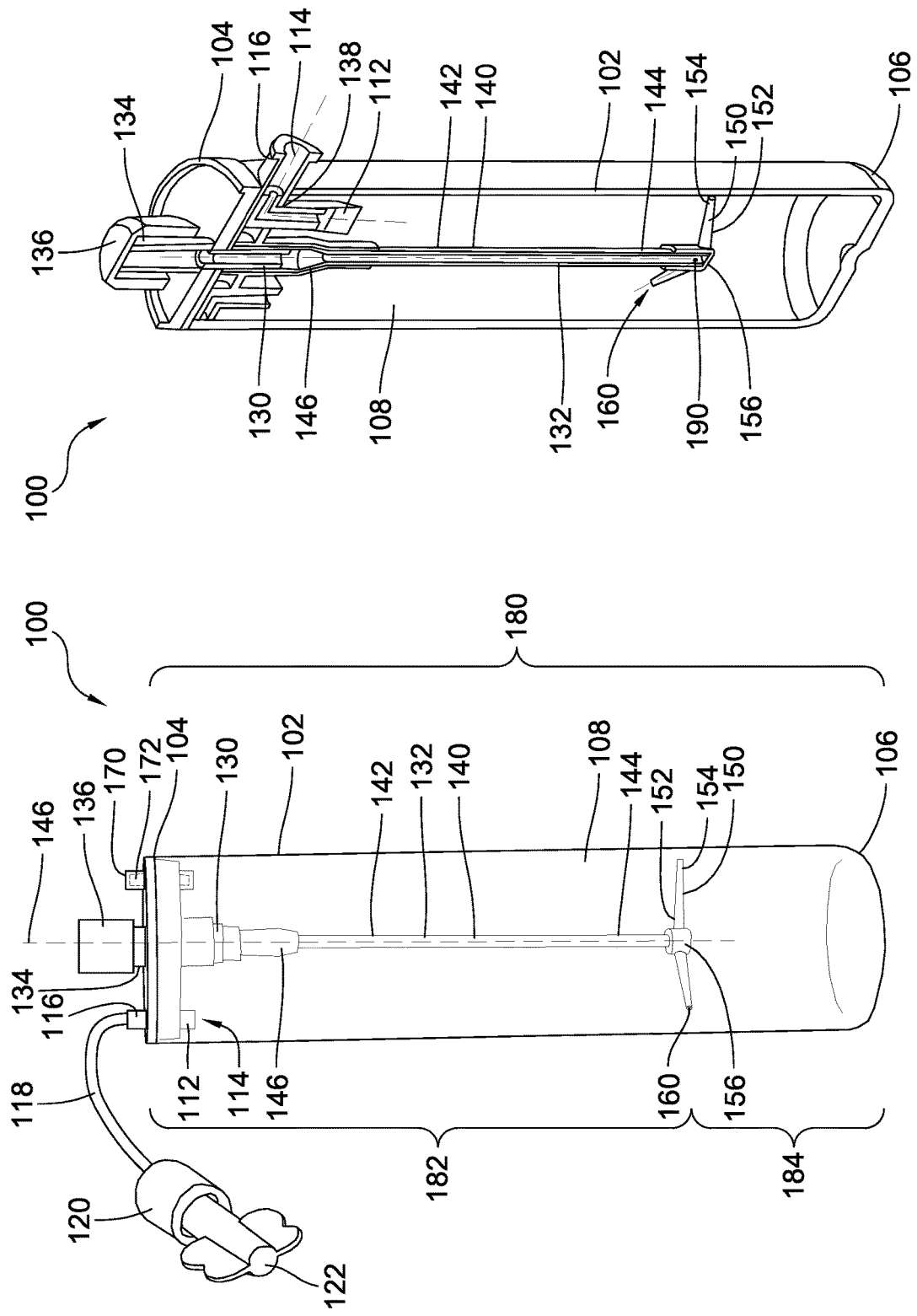

SYSTEM AND METHOD FOR SEPARATION OF BLOOD COMPONENTS

BACKGROUND

Many clinicians (e.g., veterinarians and physicians) have reported success using platelet-rich plasma (PRP) for various indications, for example to facilitated wound healing. Platelets contain various growth factors such as platelet-derived growth factor (PDGF), transforming growth factor β (TGF-β), and vascular endothelial growth factor (VEGF). PRP is a platelet rich plasma composition obtained by separating components of whole blood. Traditionally PRP is obtained from whole blood by centrifugation to remove red blood cells. Sometimes multiple centrifugation steps are required using traditional methods to obtain a suitable PRP composition.

In many instance PRP compositions are formed using blood autologous to the target patient, meaning the patient's own blood is collected and processed to form a PRP composition. In these instances, it is often impractical to utilize a heavy and expensive laboratory equipment such as a centrifuge to prepare a PRP composition.

A need therefore exists for new and improved systems and methods for preparation of PRP.

SUMMARY

In certain aspects, the present invention provides unique systems and methods for isolating platelet rich plasma form biological tissue samples. In accordance with some forms of the disclosed systems and methods, provide rapid separation of blood components without the need for centrifugation. Accordingly, in one embodiment, the present disclosure provides a method for isolating platelet rich plasma, the method comprising combining a liquid tissue sample with a polymer composition, the polymer composition comprising polyethylene glycol, wherein said combining is effective to cause formation of a supernatant comprising platelet rich plasma and a sediment comprising red blood cells. In certain embodiments, the polymer composition further comprises a saline solution. In some forms, the polyethylene glycol is present in the polymer composition at about 5 mg/ml. In accordance with certain inventive variants, the liquid tissue sample comprises whole blood. In certain embodiments, the liquid tissue sample includes an anticoagulant.

In another embodiment, the present disclosure provides a device for isolating platelet rich plasma from a liquid tissue sample, the device comprising: a container for receiving a liquid tissue sample, the container formed by one or more elongate walls defining a chamber extending from a first closed end opposing a second closed end; an inlet opening defining an inlet fluid path into the chamber, the inlet adapted to receive a liquid tissue sample into the chamber; an outlet opening defining an outlet fluid path, the outlet fluid path extending from the outlet opening to a withdrawal opening within the chamber, the outlet opening positioned at the first end of the container; an outlet tube extending from a proximal end affixed to the outlet opening to a distal end extending towards the second end of the container, wherein the outlet fluid path is further defined by the outlet tube, and wherein the withdrawal opening is positioned within the chamber spaced between the first end and the second end of the container; and one or more spindles extending from the outlet tube. In some forms, the one or more spindles extend from the distal end of the outlet tube. In certain embodiments, the outlet fluid path is further defined by a hub attached to the distal end of the outlet tube, wherein the spindles extend from the hub. In accordance with certain inventive variants, the outlet fluid path extends through at least one of the spindles.

Further forms, objects, features, aspects, benefits, advantages, and embodiments of the present invention will become apparent from a detailed description and drawings provided herewith.

BRIEF DESCRIPTION OF THE DRAWINGS

FIG. 1 is a perspective view of one embodiment of a device for isolating platelet rich plasma.

FIG. 2 is a cut-away perspective view of one embodiment of a device for isolating platelet rich plasma.

DESCRIPTION OF THE SELECTED EMBODIMENTS

Figure 3:
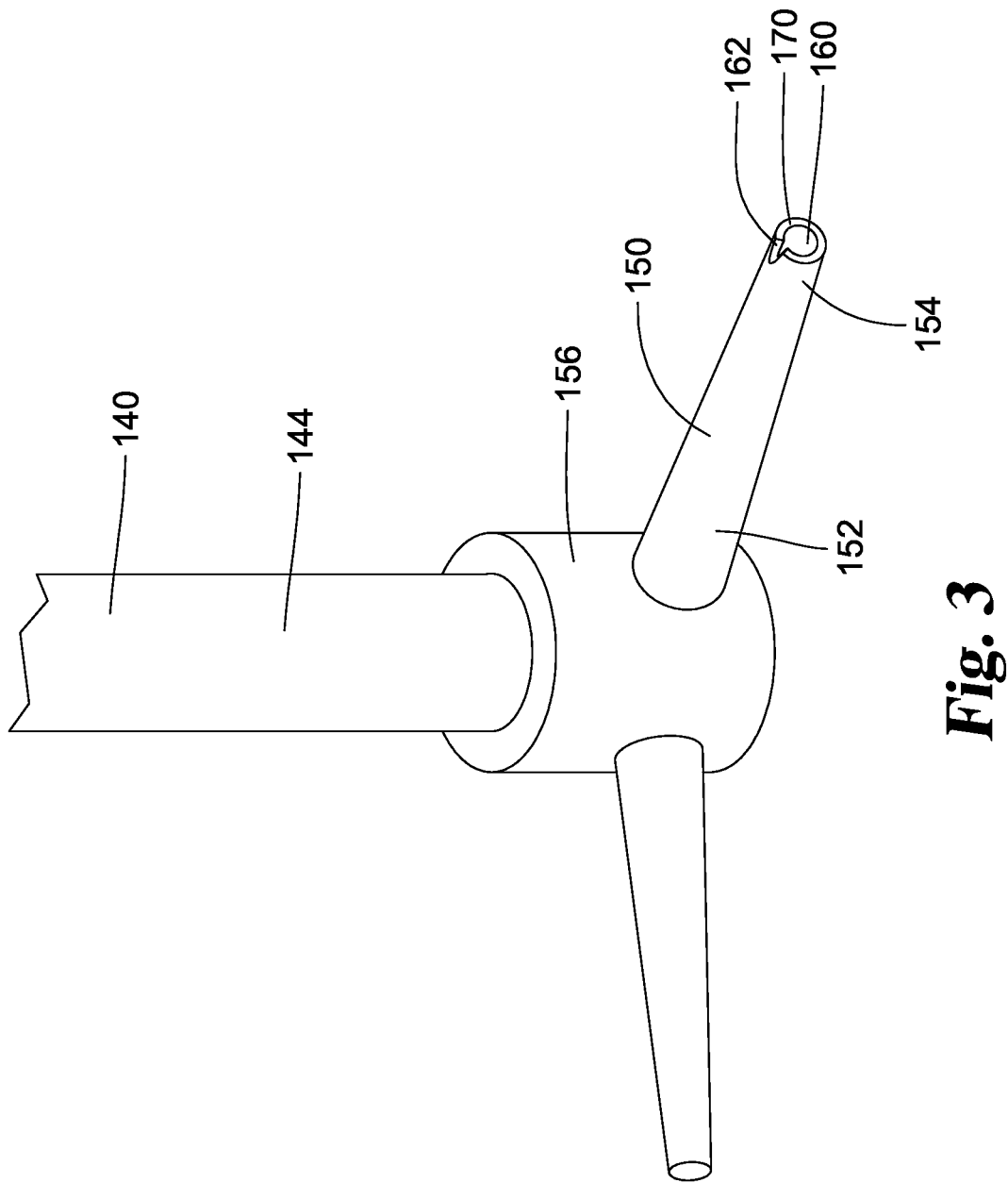
FIG. 3 is a perspective view of a portion of a device for isolating platelet rich plasma.

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates. One embodiment of the invention is shown in detail; although it will be apparent to those skilled in the relevant art that some features that are not relevant to the present, invention may not be shown for the sake of clarity.

In general, the present disclosure provides method for isolating a platelet-rich plasma (PRP) composition from a liquid tissue source. The present inventors surprisingly discovered that certain polymer compositions may be added to a platelet containing liquid source to quickly and efficiently separate a platelet rich plasma component. Suitable platelet containing liquid tissue sources may be any biological fluid containing platelets including but not limited to: whole blood, bone marrow, and/or stromal vascular fraction from adipose tissue. In certain embodiments, the liquid tissue source may include additional components such as an anticoagulant.

As discussed herein, the present disclosure provides polymer compositions suitable for addition to a platelet containing liquid source. In some forms, the polymer composition comprises polyethylene glycol (PEG) and/or pharmacologically acceptable salts thereof. As a pharmacologically acceptable salt in this invention, for example, an alkali metal salt such as sodium salt or potassium salt, an alkali earth metal salt such as magnesium salt or calcium salt, a salt formed from inorganic bases such as ammonium salt, or a salt from organic bases such as a diethanolamine salt, cyclohexylamine salt or amino acid salt can be selected for use. As used herein the term PEG encompasses compounds of various molecular weights with the structure of Compound 1 illustrated below, including polyethylene oxide (PEO) and/or polyoxyethylene (POE).

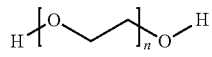

Compound 1

In certain embodiments, the PEG of the present disclosure will have an average molecular weight in the range of 4 kDa to 200 kDa, preferably 8 kDa to 150 kDa, more preferably 15 kDa to 125 kDa, even more preferably 35 kDa to 100 kDa. In certain embodiments, the methods and/or compositions of the present disclosure comprise PEG having an average molecular weight of greater than 8 kDa, preferably greater than 25 kDa. In some forms, the methods and/or compositions of the present disclosure comprise PEG having an average molecular weight of about 35 kDa. In some forms, the methods and/or compositions of the present disclosure comprise PEG having an average molecular weight of about 100 kDa.

In certain embodiments, the present disclosure provides for compositions and methods of making compositions comprising PEG and a biological fluid. In accordance with some forms, the PEG may be present in such compositions at about 0.25 mg/ml to about 50 mg/ml, preferably about 0.5 mg/ml to about 25 mg/ml, even more preferably 1 mg/ml to about 5 mg/ml. In accordance with some forms, the concentration of PEG is about 2.5 mg/ml when mixed with the biological fluid.

The present disclosure provides for biological compositions comprising a platelet rich plasma retaining a significant portion of native blood components. For example in some forms the present disclosure provides for platelet rich plasma derived from a liquid tissue source having one or more of the following native components: white blood cells, neutrophils, lymphocytes, monocytes, blast cells, eosinophils, basophils, red blood cells, and/or hemoglobin. In some forms the present disclosure provides for compositions, devices and methods for obtaining such, which retain a portion of certain native blood components while reducing a portion of other native blood components.

In some forms, the platelet rich plasma compositions of the present disclosure retain at least 25% of the native white blood cells of the liquid tissue source, preferably at least 35% of the native white blood cells of the liquid tissue source, even more preferably at least 45% of the native white blood cells of the liquid tissue source. In certain embodiments, the platelet rich plasma compositions of the present disclosure retain about 38% to about 59% of the native white blood cells of the liquid tissue source.

In some forms, the platelet rich plasma compositions of the present disclosure retain at least 25% of the native neutrophils of the liquid tissue source, preferably at least 35% of the native neutrophils of the liquid tissue source, even more preferably at least 45% of the native neutrophils of the liquid tissue source. In certain embodiments, the platelet rich plasma compositions of the present disclosure retain about 43% to about 72% of the native neutrophils of the liquid tissue source.

In some forms, the platelet rich plasma compositions of the present disclosure retain at least 25% of the native lymphocytes of the liquid tissue source, preferably at least 30% of the native lymphocytes of the liquid tissue source, even more preferably at least 35% of the native lymphocytes of the liquid tissue source. In certain embodiments, the platelet rich plasma compositions of the present disclosure retain about 32% to about 43% of the native lymphocytes of the liquid tissue source.

In some forms, the platelet rich plasma compositions of the present disclosure retain at least 25% of the native monocytes of the liquid tissue source, preferably at least 30% of the native monocytes of the liquid tissue source, even more preferably at least 35% of the native monocytes of the liquid tissue source. In certain embodiments, the platelet rich plasma compositions of the present disclosure retain about 31% to about 47% of the native monocytes of the liquid tissue source.

In some forms, the platelet rich plasma compositions of the present disclosure retain at least 20% of the native blast cells of the liquid tissue source, preferably at least 25% of the native blast cells of the liquid tissue source, even more preferably at least 30% of the native blast cells of the liquid tissue source. In certain embodiments, the platelet rich plasma compositions of the present disclosure retain about 26% to about 43% of the native blast cells of the liquid tissue source.

In some forms, the platelet rich plasma compositions of the present disclosure retain at least 25% of the native eosinophils of the liquid tissue source, preferably at least 40% of the native eosinophils of the liquid tissue source, even more preferably at least 50% of the native eosinophils of the liquid tissue source. In certain embodiments, the platelet rich plasma compositions of the present disclosure retain about 42% to about 71% of the native eosinophils of the liquid tissue source.

In some forms, the platelet rich plasma compositions of the present disclosure retain at least 40% of the native basophils of the liquid tissue source, preferably at least 50% of the native basophils of the liquid tissue source, even more preferably at least 60% of the native basophils of the liquid tissue source. In certain embodiments, the platelet rich plasma compositions of the present disclosure retain about 30% to about 97% of the native basophils of the liquid tissue source.

In some forms, the platelet rich plasma compositions of the present disclosure retain 3% or less of the native red blood cells of the liquid tissue source, preferably 1% or less of the native red blood cells of the liquid tissue source, even more preferably 0.5% or less of the native red blood cells of the liquid tissue source. In certain embodiments, the platelet rich plasma compositions of the present disclosure retain about 0.2% to about 0.8% of the native red blood cells of the liquid tissue source.

In some forms, the platelet rich plasma compositions of the present disclosure retain 3% or less of the native hemoglobin of the liquid tissue source, preferably 1% or less of the native hemoglobin of the liquid tissue source, even more preferably 0.75% or less of the native hemoglobin of the liquid tissue source. In certain embodiments, the platelet rich plasma compositions of the present disclosure retain about 0.3% to about 0.9% of the native hemoglobin of the liquid tissue source.

In some forms, the platelet rich plasma compositions of the present disclosure retain at least 50% of the native platelets of the liquid tissue source, preferably at least 65% of the native platelets of the liquid tissue source, even more preferably at least 75% of the native platelets of the liquid tissue source. In certain embodiments, the platelet rich plasma compositions of the present disclosure retain about 52% to about 98% of the native platelets of the liquid tissue source.

In some forms, the present disclosure provides a device for isolating platelet rich plasma from a liquid tissue sample. In accordance with certain embodiments, the device comprises a rigid or semi-rigid tube or vial. The device of the present disclosure may comprise any material suitable for receiving and storing a biological tissue sample. Thus in accordance with certain embodiments, the container may contain an inlet fitting defining an opening into the container, the inlet fitting positioned at one end of the container. The inlet fitting defining an inlet fluid path. In some forms, the container may include an outlet fitting, and an outlet tube attached thereto. In certain embodiments, the outlet tube is formed as one piece with the outlet fitting. The outlet tube is positioned within the container and extends from the outlet fitting towards the opposite (distal) end of the device. In some forms, an outlet opening is provided at or near the distal end of the outlet tube. In this way, a portion of the sample may be withdrawn, specifically the sample portion between the outlet fitting and outlet opening, while leaving a portion of the sample between the outlet opening and the distal end of the container. Thus in accordance with certain embodiments, an outlet fluid path is defined which flows at least through the outlet tube and outlet fitting.

In certain embodiments, the container comprises one or more spindles extending from the outlet tube, and/or a hub attached to the outlet tube. In certain embodiments the spindles are configured to extend away from the central axis of the outlet tube and towards the side walls of the contain, in this way the spindles ensure that the outlet tube remain roughly centered within the container and away from the outer walls of the container to facilitate sample withdrawal. In certain embodiments one or more of the spindles is hollow and includes an outlet opening to allow sample withdrawal through the spindle. In this way, in certain embodiments the outlet fluid path may extend through one or more of the spindles, and one or more outlet opening may be positioned on one or more of the spindles.

The container of the present disclosure may be any suitable size for obtaining a platelet rich plasma of a desired volume. For example, in some forms the container has a total volume of 500 ml, 400 ml, 300 ml, 250 ml, 200 ml, 150 ml, 100 ml, and/or 50 ml. In certain preferred embodiments, the container has a total volume of less than about 50 ml, preferably less than about 40 ml.

With reference to FIGS. 1 and 2, illustrated are representative embodiments of a device for isolating a platelet rich plasma from a liquid tissue source. The device includes a container 100 suitable for receiving a liquid sample, the container comprising wall 102 first closed end 104, and second closed end 106. The container thus defines a chamber 108 having a total volume 180. The illustrated embodiments further comprises an inlet opening 112, defining at least a portion of an inlet fluid path 114 into the chamber. In the illustrated embodiment, the inlet fluid path is further defined by an inlet fitting 116 configured to receive a liquid tissue sample. The inlet fitting may comprise any suitable configuration such as a taper lock or needle septum. In certain embodiments, the inlet fitting comprises a LUER lock attachment. In certain embodiments, the inlet fitting may be configured to receive a length of tubing 118. The embodiment illustrated in FIG. 1 further includes an inlet port 120 attached to the tubing and including a removable inlet cap 122. In the embodiment illustrated in FIG. 2 the inlet opening extends from the sidewall of the container, in this way the inlet fluid path includes a bend 138.

In certain embodiments, the device includes an outlet opening 130, the outlet opening at least partially defining an outlet fluid path 132, and positioned at or near the first end of the container. In the illustrated embodiment the outlet fluid path is further defined by an outlet fitting 134 configured for withdrawal of at least a portion of the liquid tissue sample from the container. In certain embodiments, the outlet fitting comprises a LUER lock attachment; in certain embodiments, the outlet fitting may be configured to receive a length of tubing. In some forms, the disclosed device includes a capping member 136; the capping member may be removably engaged to said outlet fitting to prevent contamination of the outlet fluid path. In some forms, the disclosed device includes an outlet tube 140 extending from a proximal end 142 operably attached to the outlet opening, to a distal end 144 extending towards the second end of the container. In some forms, a tube fitting 146 is configured to facilitate attachment of the outlet tube to the outlet opening.

In certain embodiments, the device includes one or more spindles 150. The spindles are configured to extend away from a central axis 146 of the outlet tube. The spindle(s) having a distal end 154 extending from proximal end 152. In certain embodiments, the device further comprises a hub 156, attached to the distal end of the outlet tube, wherein the proximal ends of the one or more spindles are attached to the hub. It is also envisioned that the spindles may be directly attached to or contiguous with the outlet tube. While the illustrated embodiment shows spindles at only the distal end of the outlet tube it is also envisioned that spindles and/or hubs may be placed at any point along the length of the outlet tube.

The device further comprises at least one withdrawal opening 160. In the illustrated embodiment, the withdrawal opening is shown at or near the distal end of the spindle. As disclosed, herein the withdrawal opening can be positioned along the length of one or more spindles, at the hub, and/or on the outlet tube. In this way, the outlet fluid path extends between the outlet opening and the outlet fitting, and may extend through one or more spindles, hub member, outlet tube, outlet opening, and/or outlet fitting. In accordance with certain inventive variants, one or more ports 190 define an opening between a hollow spindle and the hub and/or outlet tube.

In certain embodiments, the device may include a vent tube 170, configured to release pressure during filing and/or withdrawal of sample from the chamber. In some forms, a filter 172 is disposed within the vent tube.

With reference to FIG. 3, shown is a perspective view of one embodiment of the distal portion of the outlet tube. The illustrated embodiment includes notch 162, defining a portion of spindle wall 170 removed near the withdrawal opening and configured to prevent formation of a pressure vacuum upon sample withdrawal.

In use, a liquid tissue sample (e.g. anti-coagulated blood) is mixed with a polymer composition comprising polyethylene glycol. The liquid tissue sample and polymer composition may be mixed prior to introduction into the container described herein, or the liquid tissue sample and polymer composition may be mixed within the container. In some forms, the polymer composition causes the red blood cell portion of the liquid tissue sample to settle within about 15 to 30 minutes, leaving a platelet rich plasma layer on top of a red blood cell layer. In preferred embodiments, the polymer composition causes the red blood cell portion of the liquid tissue sample to settle within about 15 minutes or less, leaving a platelet rich plasma layer on top of a red blood cell layer. The outlet tube of the present design is configured so that the withdrawal opening is within the platelet rich plasma layer, above the red blood cell portion. In this way, the total volume 180 of the container is divided into a first portion 182, above the withdrawal opening extending between the withdrawal opening and the first end of the container, and a second portion 184 below the withdrawal opening extending between the withdrawal opening and the second end of the container. In certain embodiments, the present design allows for efficient withdrawal of the sample contained in the first portion without disruption of the sample contained in the second portion.

For the purpose of promoting further understanding of aspects of the present disclosure and their features and advantages, the following specific examples are provided. It will be understood that these examples are illustrative, and not limiting, of embodiments of the present disclosure.

EXAMPLES

Example 1

Isolation of Platelet Rich Plasma from Whole Blood 250 mg of PEG 35 kDa was diluted with 10 ml isotonic saline solution. The diluted composition was mixed until fully solubilized to make a 25 mg/ml PEG 35 kDa solution. 250 mg of PEG 100 kDa was diluted with 10 ml isotonic saline solution. The diluted composition was mixed until fully solubilized to make a 25 mg/ml PEG 100 kDa solution. 12 ml syringes were loaded with 1 ml of either the 25 mg/ml PEG 35 kDa solution or the 25 mg/ml PEG 100 kDa solution. Additional 12 ml syringes were loaded with 8 ml of freshly drawn blood, with 1 ml of Anticoagulant Citrate Dextrose Solution (ACD-A) using standard phlebotomy techniques. Luer-to-Luer connectors were used to connect each blood-containing syringe to a syringe containing either the 25 mg/ml PEG 35 kDa solution or the 25 mg/ml PEG 100 kDa solution. For each set of syringes, the PEG solutions were mixed with the blood resulting in a solution containing 2.5 mg/ml PEG. The empty syringe was discarded and the loaded syringed were further mixed by inverting each syringe at least 5 times before being left to stand upright for 15 minutes. After 15 minutes, a platelet rich plasma layer had formed leaving a sediment red blood cell layer After 15 minutes a new syringe was attached to each syringe and used to withdraw the platelet rich plasma layer. Each of the samples were tested and confirmed for >50% platelet recovery in less than or equal to 15 minutes.

Example 2

Comparison of 8 kDa PEG and 35 kDa PEG 250 mg of PEG 8 kDa was diluted with 10 ml isotonic saline solution (Hanks Balanced Salt Solution) and placed on a rocker until fully solubilized to make a 25 mg/ml PEG 8 kDa solution. 250 mg of PEG 35 kDa was diluted with 10 ml isotonic saline solution (Hanks Balanced Salt Solution) and placed on a rocker until fully solubilized to make a 25 mg/ml PEG 35 kDa solution. 5 mg/ml solutions were prepared by further diluting each of the 25 mg/ml solutions into 8 ml of isotonic saline solution. Blood was drawn from three donors and mixed with Anticoagulant Citrate Dextrose Solution (ACD-A) (110 ml blood mixed with 10 ml ACD-A). 9 ml of blood was mixed with 1 ml of either the 5 mg/ml PEG 8 kDa solution or the 5 mg/ml PEG 35 kDa solution, resulting in a final PEG concentration of 0.5 mg/ml. The mixed samples were left to stand for 15 minutes in 12 ml syringes.

Syringes containing the PEG 8 kDa did not form a plasma layer, thus no platelet rich plasma could be harvested.

A plasma layer formed in each of the PEG 35 kDa samples. The plasma layer of each PEG 35 kDa sample was extracted and a Complete Blood Count (CBC) analysis was performed in triplicate on baseline blood and platelet concentrates. The percent cell recoveries for the PEG 35 kDa samples are shown in Table 1 below. The results of this study show that not all molecular weights of PEG can rapidly from a platelet rich plasma.

|  | PEG 35 kDa | Standard Deviation |
|---|---|---|
| White Blood Cell | 48.4% | 10.5% |
| Neutrophil | 57.2% | 14.3% |
| Lymphocyte | 37.1% | 5.3% |
| Monocyte | 39.2% | 8.0% |
| Blast Cell | 34.7% | 8.4% |
| Eosinophil | 56.3% | 14.4% |
| Basophil | 63.2% | 33.4% |
| Red Blood Cell | 0.5% | 0.3% |
| Hemoglobin | 0.6% | 0.3% |
| Hematocrit | 0.3% | 0.4% |
| Platelets | 75.1% | 22.5% |

While the invention has been illustrated and described in detail in the drawings and foregoing description, the same is to be considered as illustrative and not restrictive in character, it being understood that only the preferred embodiment has been shown and described and that all changes, equivalents, and modifications that come within the spirit of the inventions defined by following claims are desired to be protected. All publications, patents, and patent applications cited in this specification are herein incorporated by reference as if each individual publication, patent, or patent application were specifically and individually indicated to be incorporated by reference and set forth in its entirety herein.

The invention claimed is:

1. A device for isolating platelet rich plasma from a liquid tissue sample, the device comprising:
   a container for receiving a liquid tissue sample, said container formed so as to define a chamber extending from a first closed end opposing a second closed end;
   an inlet opening defining an inlet fluid path into said chamber, said inlet opening adapted to receive a liquid tissue sample into said chamber;
   an outlet opening defining an outlet fluid path, said outlet opening positioned at said first closed end of said container;
   an outlet tube extending from a proximal end affixed to said outlet opening to a distal end extending towards said second closed end of said container, wherein said outlet fluid path is at least partially defined by said outlet tube; and
   a plurality of spindles extending from the distal end of said outlet tube, the spindles being hollow and each defining a withdrawal opening at an end thereof such that the outlet fluid path extends from said outlet opening to each withdrawal opening via the outlet tube, wherein each withdrawal opening is positioned within said chamber spaced between said first closed end and said second closed end of said container, the spindles having a notch near the withdrawal opening.

2. The device of claim 1, wherein said outlet fluid path is further defined by a hub attached to said distal end of said outlet tube, wherein said spindles extend from said hub.

3. The device of claim 1, wherein said outlet tube extends into said chamber at or near a central axis of the chamber.

4. The device of claim 1, wherein said container has a volume of less than 40 ml.

5. The device of claim 1, comprising a vent tube extending from the chamber through the first closed end.

6. A method for isolating platelet rich plasma, the method comprising:
   adding a starting composition comprising a liquid tissue sample and a polymer composition to a container as described in claim 1, wherein the starting composition is allowed to separate into a first layer comprising plasma, and a second layer comprising red blood cells; and withdrawing the first layer through the outlet opening.

7. The method of claim 6, wherein the liquid tissue sample comprises red blood cells and plasma and the polymer composition comprises polyethylene glycol.

* * * * *